(12) United States Patent
Amling et al.

(10) Patent No.: US 9,841,280 B2
(45) Date of Patent: Dec. 12, 2017

(54) MODULAR MEDICAL IMAGING SYSTEM

(71) Applicant: Karl Storz Imaging, Inc., Goleta, CA (US)

(72) Inventors: Marc R. Amling, Santa Barbara, CA (US); Timothy King, Goleta, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 585 days.

(21) Appl. No.: 13/731,395

(22) Filed: Dec. 31, 2012

(65) Prior Publication Data

US 2014/0184766 A1 Jul. 3, 2014

(51) Int. Cl.
*A61B 1/00* (2006.01)
*G01C 11/04* (2006.01)
*A61B 1/04* (2006.01)

(52) U.S. Cl.
CPC ............ *G01C 11/04* (2013.01); *A61B 1/0005* (2013.01); *A61B 1/00009* (2013.01); *A61B 1/00039* (2013.01); *A61B 1/00105* (2013.01); *A61B 1/04* (2013.01)

(58) Field of Classification Search
None
See application file for complete search history.

(56) References Cited

U.S. PATENT DOCUMENTS

| | | | |
|---|---|---|---|
| 6,960,161 B2 | 11/2005 | Amling et al. | |
| 7,212,227 B2 | 5/2007 | Amling et al. | |
| 7,316,646 B2 | 1/2008 | Amling et al. | |
| 7,471,310 B2 | 12/2008 | Amling et al. | |
| 7,520,853 B2* | 4/2009 | Amling | A61B 1/00059 348/207.11 |
| 7,821,530 B2 | 10/2010 | Amling et al. | |
| 7,855,727 B2 | 12/2010 | Adler et al. | |
| 8,059,160 B2 | 11/2011 | Shinozaki et al. | |
| 8,089,509 B2 | 1/2012 | Chatenever et al. | |
| 8,199,188 B2 | 6/2012 | Amling et al. | |
| 8,274,559 B2 | 9/2012 | Amling et al. | |
| 2004/0028390 A9* | 2/2004 | Chatenever | H04N 5/232 386/224 |
| 2006/0152516 A1* | 7/2006 | Plummer | 345/538 |
| 2007/0024717 A1* | 2/2007 | Chatenever | A61B 1/042 348/211.99 |
| 2010/0295870 A1* | 11/2010 | Baghdadi et al. | 345/650 |
| 2011/0029733 A1 | 2/2011 | Adler et al. | |
| 2012/0013755 A1 | 1/2012 | Shinozaki et al. | |

* cited by examiner

*Primary Examiner* — Kevin McInnish
(74) *Attorney, Agent, or Firm* — Whitmyer IP Group LLC (57) ABSTRACT

A modular video imaging system, and more particularly, a modular video imaging system having a control module connectable to multiple input modules. The input modules each capable of receiving differing types of image data from different types of cameras and processing the image data into a format recognizable by the control module. The control unit providing general functions such as user interface and general image processing that is not camera specific.

32 Claims, 3 Drawing Sheets

MODULAR MEDICAL IMAGING SYSTEM

FIELD OF THE INVENTION

The invention relates to a modular medical imaging system having a control module connectable to a variety of input modules and, more in particularly, the invention relates to a modular system where the control module provides general functions such as user interface and general image processing that is not camera/source specific and the input modules are capable of processing image data from many different sources and converting it into a format compatible with the control module.

BACKGROUND OF THE INVENTION

The field of endoscopy, to which the present invention relates, includes medical diagnostic and therapeutic disciplines that utilize endoscopes to view otherwise inaccessible body cavities using minimally invasive surgical procedures. Endoscopes typically include cameras located at the distal tip of the endoscopes to capture images. Endoscopic cameras are typically small and lightweight for ease of use by medical professionals.

In known systems, endoscopic cameras are typically connected to a Camera Control Unit ("CCU"), with the CCU processing and displaying the imaging data transmitted from the endoscopic camera. Often, different medical procedures require different camera types, leading to a large inventory of cameras. Additionally, each camera type must be compatible with the CCU to function correctly. As such, each CCU has software to process and operate a variety of camera technologies, and as new technologies become available, the CCU may need updated software to properly process images from new camera technology. Additionally, often the CCU hardware becomes outdated, thus requiring an entirely new CCU to process the images of both old and new camera technologies used by a physician.

CCUs may be designed to be reprogrammable and reconfigurable, and as such, an older model CCU may sometimes be upgraded or configured to work with a new camera technology. However, in many cases the older model CCU may be too outdated to update or it may be less costly to replace the older model CCU with a new one because the reconfiguring of the CCU is often a time and labor intensive process that requires the CCU be returned to the manufacturer for disassembly, installation of new components and testing. Moreover, while it may be possible to update software in older model CCUs, the existing hardware in older model CCUs may not allow for the older model CCUs to support software for newer technology image sensors and image formats provided with newly developed camera technology.

In known systems, endoscopic cameras used during endoscopic surgery are typically referred to as heads or camera heads. To achieve the desired size and weight of the camera heads, camera head and/or integrated endoscope-camera assembly electronics are typically separated physically from the majority of circuitry required to process and output high-quality, color video images. The endoscope-camera assembly electronics is typically housed in the CCU. In known systems, CCUs may be placed on or in carts, in or on ceiling boom arms, or may be permanently wall-mounted.

In known video imaging systems, a cable simply connects a camera head to a CCU. When image data is acquired, or picked up, it is sent by the camera head to the CCU through the cable. Upon receiving the image data from the camera head, the CCU processes the signal and displays the acquired image on a viewing device. Generally, the image is used by a medical professional and/or for storage on various media (video cassette recorder, floppy disk, hard drives, flash drives, compact disks, digital video disks, and the like) and/or for transmission to remote locations in various manners, such as by the Intranet, Internet, radio transmission, and the like.

The CCU may also send commands to the camera head to adjust various settings (i.e. color balance, electronic shutter for light sensitivity, and other optical and electronic characteristics).

Traditionally, CCUs are compatible with a limited number of camera heads. A CCU's hardware is usually difficult to configure for proper communication with varying types of camera heads because camera heads use varying types of imaging devices that can differ in pixel resolution, timing requirements (i.e. PAL, NTSC, Progressive, and other formats), signal output type (i.e. analog or digital), physical size, and in other characteristics.

Analog video system types differ in scanning principles, resolution capability, sampling rates, aspect ratios, synchronization, bandwidth, and the like. Moreover, video system types may differ between broadcast, closed circuit, and computer applications. Analog video systems are typically classified as either composite (luminance and chrominance components multiplexed into a single signal) or component (separate signals for each chrominance component, and synchronization signals). In broadcasting applications, composite formats are generally used. For closed circuit systems (such as video production and editing, medical, industrial, and scientific applications) component formats are typically used. The primary composite analog video standards used are primarily PAL, NTSC, and SECAM, with one specific standard used in different geographical areas.

Digital video systems are typically differentiated by their application. Advanced television (ATV), high definition television (HDTV), and computer systems may differ in format and signal characteristics. In some areas, digital video formats and standards are currently being developed and adopted. The Society of Motion Picture and Television Engineers (SMPTE) normally defines and adopts voluminous digital video formal standards. As each is adopted, various applications, and application improvements generally will also be realized. Some digital video standards currently in use are: IEEE-1394 FireWire®, ISO/IEC IS 13818, International Standard (1994), MPEG-2, and ITU-R BT.601-4 (1994) Encoding Parameters of Digital Television for Studios.

Furthermore, there may be variability from device to device of the same type, which may affect camera head performance. Additionally, commands sent from the CCU to the camera head are generally unique depending upon the camera head type being used. Moreover, as repairs, modifications, or improvements are made to camera heads, the CCU, which was originally designed to be compatible with the older camera head, may become incompatible and may require upgrading as well.

This overall variability in camera heads, either caused by imaging device technologies or by CCU command characteristics, often results in a CCU being specifically designed to be compatible with a specific camera head type. Also, consumers may desire different capabilities related to specific applications of the cameras, such as medical, industrial, and scientific uses. Capabilities include picture in picture (PIP), reverse video (image flip), electronic zoom, electronic rotation, still image capture, and stereoscopic video interface.

Moreover, CCUs are typically designed for use with camera head technologies currently in existence, and not designed to anticipate and accommodate camera heads yet to be developed. Hence, CCUs are typically not designed to be compatible with future camera head technologies; particularly, image device and image signal transmission technologies. These differences between older and newer camera heads also contribute to compatibility problems.

Because CCUs are usually compatible with limited quantities of camera heads, CCUs are typically discarded in favor of ones that were designed concurrently and/or to be compatible with particular camera head technologies. Consequently, CCUs have become an added expense often associated with changing imaging devices or camera heads. Further, it is typically desired for camera heads to be improved due to the demand from consumers to have the latest technology and advancements in equipment. Moreover, CCUs used in medical and veterinary fields are increasingly being mounted permanently in equipment bays or carts and/or permanently mounted within the walls of surgical operating rooms themselves. The expense associated with replacing CCUs to maintain compatibility with camera heads is subsequently passed onto consumers.

Thus, there exists a need for a modular imaging system that overcomes the disadvantages of the prior art. There exists a need to provide a system having a control module connectable to multiple input modules that may be connected to various camera heads and that may receive data in various formats from various camera heads. There exists a need for the input module to be connected to a control module that may be updated or reprogrammed in an efficient and cost effective manner, rather than replacing the older input module or control module with a newer module. There exists a need for the modular imaging system, including at least one input module and a control module, to be readily compatible with existing and future imaging technologies and that allows for the at least one input module and the control module to be backwards and forwards compatible.

It is also desired to configure and control features of one module from another module upon attachment of one module to another via the cable. It is also desired to control the power state of one module via the other module upon attachment of the modules via the cable.

SUMMARY OF THE INVENTION

Accordingly, it is an object of the invention to provide a modular imaging system where the image acquisition, processing, control and display chain is segmented in such a manner as to optimize adaptability and compatibility with existing and yet to be developed image sensor formats and architectures, as well as with existing and yet to be developed display technologies.

It is also an object of the invention to support increasing varieties and sub-varieties of image sensors, which require unique interfaces for compatibility with video and display signal technologies.

These and other objects of the present invention are achieved by providing a modular imaging system having a control module, a first input module connectable to the control module and a second input module connectable to the control module. The first input module configured for receiving a first type image data and processing the first type image data into processed image data and the second input module configured for receiving a second type image data and processing the second type image data into processed image data. The control module configured for receiving the processed image data from the first and second input module.

The modular imaging system may further have a third input module configured for receiving a third type image data and processing the third type image data into processed image data for transmission to the control module.

The modular imaging system may further have a fourth input module configured for receiving a fourth type image data and processing the fourth type image data into processed image data for transmission to the control module.

The types of image data between the different modules may be differentiated by aspect ratio, timing, pixel rate, pixel resolution, and pixel encoding. The types of image data may also be differentiated by being analog, digital, standard definition, high definition or a combination thereof.

The control module may be used to further manipulate the processed image data into manipulated image data to provide zoom, PIP, graphical user interface (GUI), GUI overlay on an image, printing, video and still recording, and the like. A user may also annotate the image data by drawing or typing.

The control module may be connected to a display to display the manipulated image data and/or the processed image data. The control module may also output the manipulated image data and/or the processed image data to a hard drive, a personal computer, a printer, and the like A camera may be connected to the input module for transmitting image data, and a display can be connected to the control module for displaying processed and manipulated image data. The input module can receive and process still image data and video image data from a camera head.

The input module may receive and process digital video data. The digital video data may be sent in run-time programmable images sizes, color spaces, bit-depths and framerates.

The input module may receive and processes analog video data. The analog video data may be sent in run-time programmable images sizes, color spaces, bit-depths and framerates.

The input modules may be connected to the control module via cables or wirelessly. Still further, the cameras may be connected to the input modules via cables or wirelessly.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

DETAILED DESCRIPTION OF THE INVENTION

Accordingly, the invention involves a modular medical imaging system including several modules, such as an input module and a control module, which can be developed, sold and installed at different times. For example, a system may be initially installed with a control module and several input modules, and later additional modules can be added to the system.

The system allows for later developed modules incorporating various technologies and evolving industry standard interfaces as they evolve into an endoscopic system. By having modularity between the control module and input module, manufacturers can prevent having to re-design an entire new system for newer technologies and end users can avoid purchasing entirely new systems. The system provides the ability to accommodate future imaging system improvements and adaptations as current technology limitations are overcome by adding new input modules, which are forward and backward compatible with the control module, without obsolescing initial customer investments in control modules. The system also provides the ability for a user to add a new control module to accommodate future improvements, which is forward and backward compatible with older input modules. This allows one to take advantage of new features and functions of one module without requiring redesign and/or replacement of the entire system.

For example, the industry standard in display and recording infrastructure technologies evolve at a different rate than, say, the video endoscope technology, imaging technology, or proximal camera head technology. Newer technologies often use differing imaging data and parameters, such as aspect ratio, timing, pixel rate, pixel resolution, and pixel encoding. By having an input module connected to a control module, where the input module is forward and backward compatible with the control module, new camera technologies may be provided to replace outdated camera technologies, while still being compatible with older control modules.

Thus, a user can replace existing control modules with newer control modules that allow for a display having higher resolution or more color bit depth or 3D. Similarly, a user can replace an existing input module, which only supports a limited number of camera heads, without replacing the control module or the display.

Such a system provides a competitive advantage by being able to provide newer technologies faster and uses the benefit of the backwards and forwards compatibility between the control modules and input modules.

The modular imaging system allows upgradeability and compatibility with a multitude of camera heads that are supported by a plurality of input modules, where the camera heads and input modules may be existing or yet to be developed. Formerly, when a new imaging technology became available, a CCU would not be incompatible with the new technology due to a variety of constraints, for example, outdated hardware. By using a modular architecture, the new technology can be supported by a new input module that is backward compatible with the existing control module. The modular architecture increases the likelihood that existing visualization technology and yet to be developed visualization will be able to operate with some if not all of the same image processing hardware. This results in decreased capital costs for physicians offices, surgical offices and/or hospitals.

The control module may be designed to accommodate general image processing and display functions. These general functions include, for example, supporting a separate user interface, overlaying a user interface onto an image, image capture and streaming functionality as well as input/output functionality for the display/monitor interfaces, system interface and control, and network connectivity. The control module may be designed to accommodate a single input module or multiple input modules. The control module may be connected to a display or the control module includes a display as a one piece unit. The control module may include a processor as well.

For example, a user may only wish to purchase a control module and only one input module at a time. Thus, the overall modular system can be purchased at a lower initial cost. If the consumer wishes to purchase a new camera type, the modular system can be upgraded with a new input module to support the new imaging technology. The new input module may replace the old input module or be used together with the older input module.

The input modules can support functions required for a group or family of image sources, such as cameras or auxiliary inputs. The input module can provide compatibility between the family of image sources and the control module. Over the life of the system, additional input modules may be purchased to support emerging imaging technology such as 3D imaging, advanced fluorescence imaging, solid-state variable direction of view endoscopes, wireless camera heads and so on.

The group of input modules connected to the control module may include an auxiliary input module. The auxiliary input module may support a variety of video sources such as third party camera control units, C-Arm, X-Ray, Ultrasound, Personal Computers and the like. Supported input formats may include, DVI, VGA, S-Video, Composite, 3G-SDI and the like. Inputs may be both automatically and manually selected. The auxiliary module provides increased backward compatibility, forward compatibility and third party image source compatibility.

It should be noted that as used herein, the categorization of Standard Definition (SD) or High Definition (HD) is not intended to limit the categories to a single signal format, but rather, many differing signal formats may be used. Furthermore, many different signal formats are categorized as SD and many different signal formats may be categorized as HD. For instance, SD generally refers to a line count of up to approximately 720×480 NTSC and PAL; while HD refers to systems that utilize a higher line count and may include, but is not limited to, 1280×720 progressive or 1920×1080 interlaced, which are only two of the commonly used HD resolutions. Furthermore, the modules are capable of sending digital video in the form of HD and SD video over the cable from module to module at fully run-time programmable image sizes, color spaces, bit-depths and frame-rates. The receiving and transmitting ends of the video signals can auto-negotiate these various parameters.

There are commonly used types of signal formats, however, it is contemplated that additional formats may be provided for and especially new signal formats that may become available. Two commonly used SD format types are NTSC and PAL. It should be noted that these are just two video signal formats and that there are many differing types and modifications to the above-listed types including, for example, a modified version Phase-Alternating Line (PAL-M).

In addition to the standard NTSC and PAL SD (NTSC and PAL) composite, RGB, and s-video (Y/C) outputs, numerous other outputs may be used. The following examples are presented to further illustrate and explain the present invention and should not be taken as limiting in any regard.

Serial Digital Interface (SDI), standardized in ITU-R BT.656 and SMPTE 259M, is a digital video interface used for broadcast-grade video. A related standard, known as High Definition Serial Digital Interface (HD-SDI), is standardized in SMPTE 292M and provides a nominal data rate of 1.485 Gbit/s.

Digital Visual Interface (DVI) is a video interface standard designed to maximize the visual quality of digital display devices such as flat panel LCD computer displays and digital projectors and is partially compatible with the HDMI standard in digital mode (DVI-D). The DVI interface uses a digital protocol in which the desired illumination of pixels is transmitted as binary data. When the display is driven at its native resolution, it will read each number and apply that brightness to the appropriate pixel. In this way, each pixel in the output buffer of the source device corresponds directly to one pixel in the display device.

High-Definition Multimedia Interface (HDMI) is an all-digital audio/visual interface capable of transmitting uncompressed streams. HDMI is compatible with High-bandwidth Digital Content Protection (HDCP) Digital Rights Management technology. HDMI provides an interface between any compatible digital audio/video source and a compatible digital audio and/or video monitor, such as a digital television (DTV).

The modular architecture of the present system allows for economical buyers to progressively upgrade their imaging technology, rather than being required to purchase a CCU that is compatible with the entire range of imagers that the buyer would wish to purchase in the future. The system allows for hardware upgrades through the modules as well as software feature upgrades. Further, the cost of ownership and upgrade, such as acquisition, back-up, and maintenance, is reduced.

Referring now to the drawings, wherein like reference numerals designate corresponding structure throughout the views.

Figure 1A:
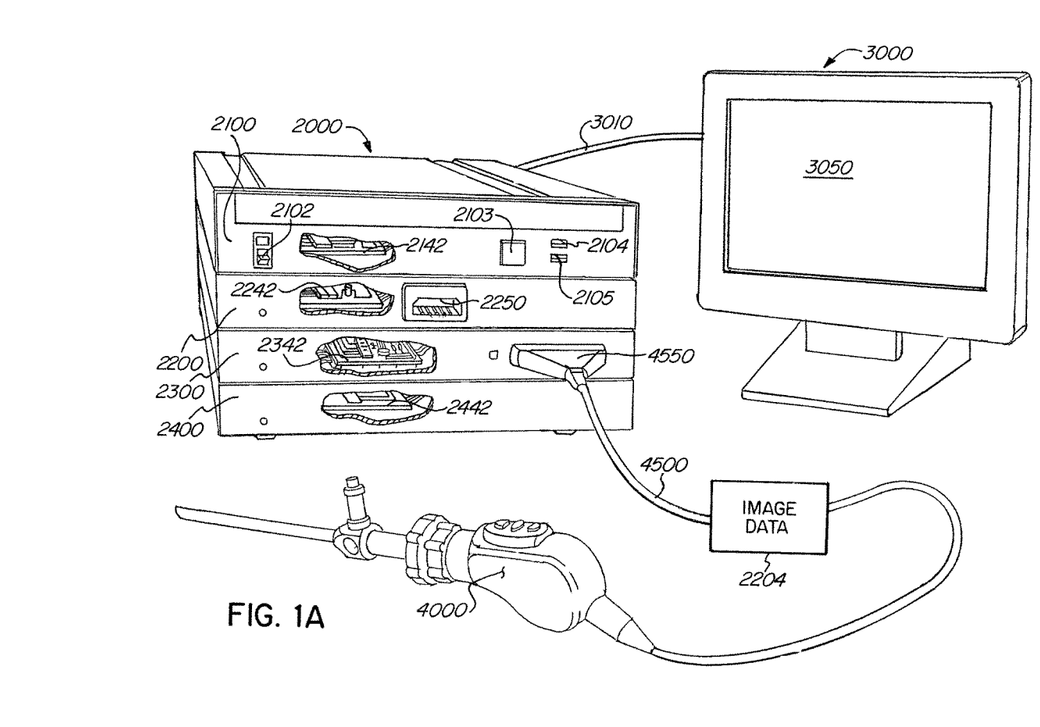
FIG. 1A is a perspective view of the front of an embodiment of the invention.

FIG. 1A shows a perspective view of the endoscopic system including input modules 2200, 2300 and 2400, and the control module 2100 stacked upon one another. Control module 2100 is shown connected to display 3000. In certain embodiments, the control module 2100 may be separate from the display 3000 and in other embodiments the control module 2100 may form a one-piece unit with the display. In certain embodiments, the display has a screen 3050, which may be a touch screen.

Internal portions of input modules 2200, 2300 and 2400 are also shown in FIG. 1A. Input module 2300 is shown having a processor 2342 that converts image data 2204 received from the camera head 4000 into processed image data that is compatible with the control module 2100. Similarly, input module 2200 is shown having a processor 2242 and input module 2400 is shown having a processor 2442. The processor 2242 and 2442 convert image data received from differing camera heads into processed image data 2500 that is compatible with the control module 2100.

Input modules 2200, 2300, and 2400 may be configured to receive and process numerous types of image data 2204. Image data 2204 may include analog data such as CCD based video endoscopes (1/6", 1/0" CCDs) (Pre-CDS analog); CMOS (post CDS analog); and/or 720p60 single chip Digital Proximal Heads (for smaller camera heads requiring less than 1080p resolution but better than Standard Definition (SD)). Image data 2204 may also be analog High Definition (HD) image data such as from 3-Chip HD CCD camera heads or digital HD image data such as from 1080p60 3chip camera heads (CMOS) or 1080p60 1chip camera heads (CMOS). Finally image data 2204 may also be advanced fluorescence imaging, solid-state variable direction of view endoscopes, wireless camera heads and so on.

The camera head 4000 is connected to input module 2300 by a cable 4500. Cable 4500 has a connector 4550 that connects into a slot such as shown in input module 2200 as slot 2250. Camera head 4000 may send image data 2204 to the input module through the cable 4500.

Control module 2100 is shown having an on/off switch 2102, which, in certain embodiments, can control the power of all of the input modules 2200, 2300 and 2400. Control module 2100 is also shown having input slots or ports 2104 and 2105 as well as a white balance control switch 2103.

Figure 1B:
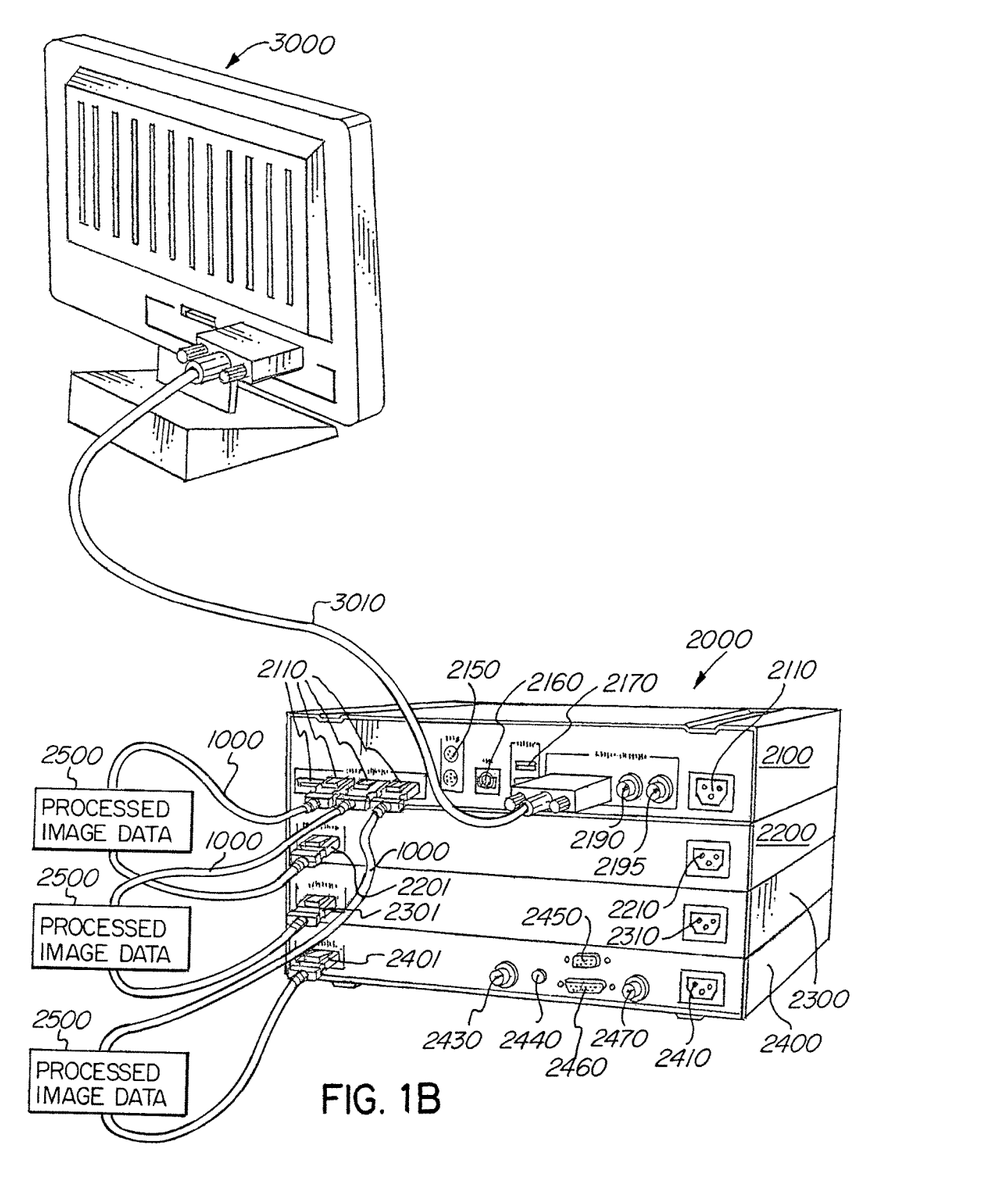
FIG. 1B is a rear perspective view of FIG. 1A.

FIG. 1B shows control module 2100 being connected to input modules 2200, 2300 and 2400 via cables 1000. FIG. 1B also shows display 3000 connected to control module 2100 via cable 3010.

FIG. 1B shows input modules 2200, 2300 and 2400 each having a power plug 2210, 2310 and 2410 respectively. Each input module may have one or more integral power supplies to support an ever increasing variety of camera heads and their unique power requirements. Control module 2100 is shown having four slots 2110 for receiving cables 1000. Control module 2100 also has various connection elements 2150, 2160, 2170, 2190 and 2195 to connect to various other devices including input and output devices. Such input/output devices may include printers, external storage devices, personal computers, local area networks, light sources, keyboards, and/or ACC port adapters. Other example input/output elements may include DVI output for DVI monitors or recorders, 3G SDI outputs for 3G SDI monitors or recorders Input modules 2200, 2300 and 2400 each have a slot 2201, 2301, 2401 respectively for receiving the cable 1000 which transfers information between the input modules and the control module 2100, such as processed image data 2500. Input module 2400 has various input and output elements 2430, 2440, 2450, 2460 and 2470 to connect to various other input and output devices. Such input/output devices may include existing or third-party CCUs, C-Arm, X-Ray, Ultrasound, and personal computers. Such inputs may also include DVI, VGA, S-Video, Composite, 3G-SDI. Other additional input and output elements may be envisioned for the various input modules 2200, 2300 and 2400.

Figure 2:
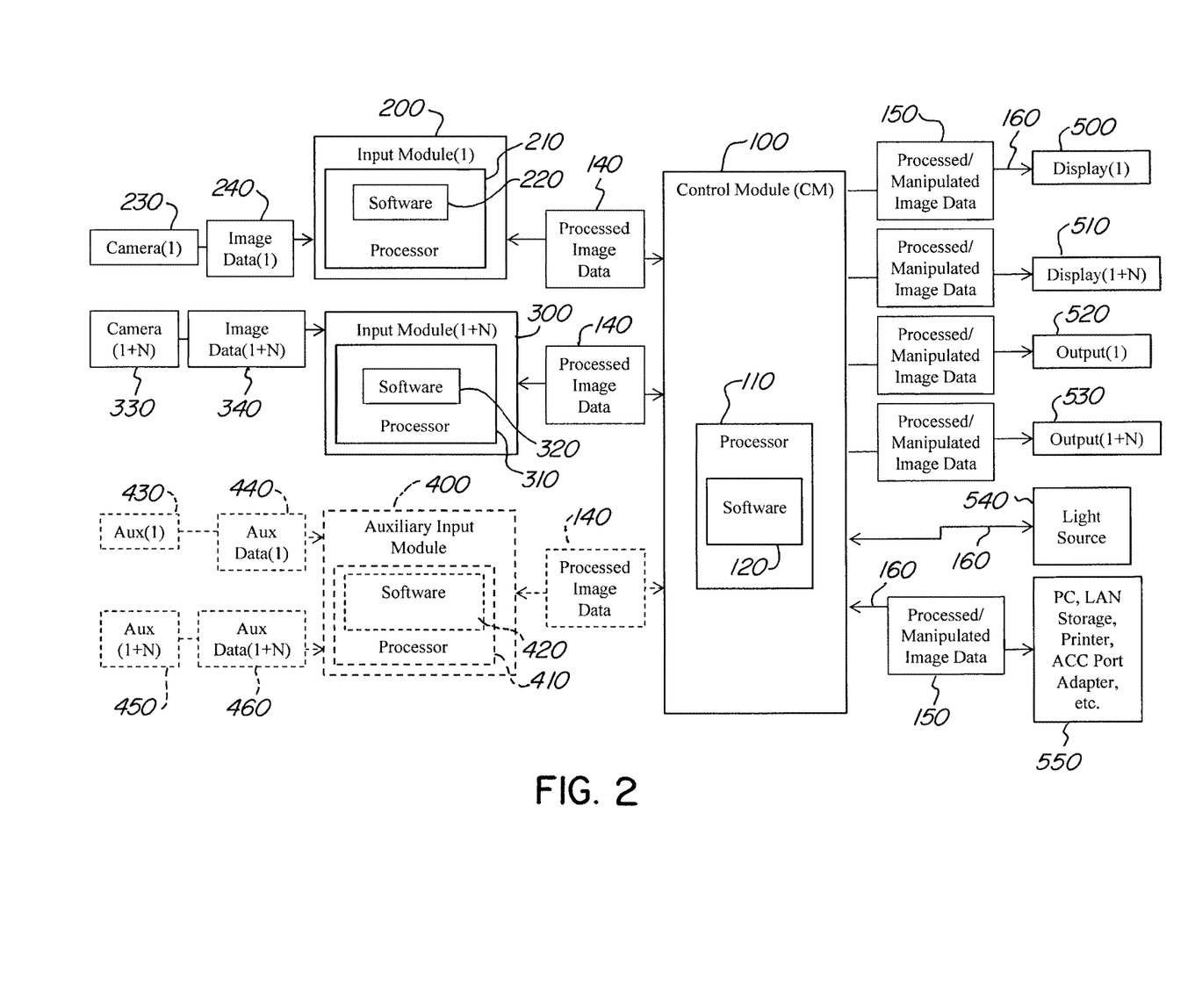
FIG. 2 is a schematic of the invention shown in FIGS. 1A and 1B.

FIG. 2 is a schematic of a modular medical imaging system that may be used, for example, in a hospital. The system has a control module 100 that can be connected to multiple input modules 200, 300, 400 that support different types of image data 240, 340, 440, 460 and process the image data 240, 340, 440, 460 into processed image data 140 which is a format compatible with the control module 100. The control module then handles functions not specific to the image data 240, 340, 440, 460 such as general image processing and outputs processed and/or manipulated image data 150 to a display/output 500, 510, 520, 530, 550.

More specifically, in this system camera(1) 230 and camera(1+N) 330 output different types of image data, image data(1) 240 and image data(1+N) 340 respectively. Therefore, input module(1) 200 receives image data(1) 240 and processes it into processed image data 140 to be sent to the control module 100. Camera(1+N) 330 is not compatible with input module(1) 200 so it is connected to input module (1+N) 300, which supports image data(1+N) 340. Input module(1+N) 300 receives image data(1+N) 340 and processes it into processed image data 140 to be sent to the control module 100.

It should be understood that input module 200, 300, 400 can be configured to receive multiple types of image data. Furthermore, image data may be for a single type of camera or a family of cameras. It should also be understood that the input modules may process the image data through hardware or software or some combination of hardware and software. For instance, input module(1) can implement a processor 210 running software 220 to process image data(1) 240 into processed image data 140. Similarly, input module(1+N) can implement a processor 310 running software 320 to process image data(1+N) 340 into processed image data 140.

The system may also implement an auxiliary input module 400, which can support multiple auxiliary devices. In this case, Aux(1) 430 outputs Aux Data(1) 440 that is received by the auxiliary input module 400 and processed into processed image data 140. Aux(1+N) 450 outputs aux data(1+N) 460 that is received by the auxiliary input module 400 and processed into processed image data 140. It should also be understood that the auxiliary input module 400 may process the image data through hardware or software or some combination of hardware and software. In one embodiment, auxiliary input module 400 can implement a processor 410 running software 420 to process image data 440, 460 into processed image data 140.

It should be under stood that terms input module and auxiliary input module can be used interchangeably as the purpose of the input/auxiliary modules is to process differing types of image data into a standard format for the control module 100. It should also be understood that while FIG. 2 shows each input module 200, 300, 400 being connected to the control module 100 with a cable 130, that the input modules and control module 100 can be wirelessly connected.

Control module 100 receives processed image data 140 from either all or some of the input modules 200, 300, 400 and can carry out general image processing, user interface and connect with various outputs. For instance, the control module 100 can connect to a touch screen display which provides a user interface through which to control the module. The control module can further process the processed image data 140 and transmit the process/manipulated image data 150 to various places, such as displays 500, 510, outputs 520, 530, PCs, LANs, Storage devices, printers, ACC Port Adapters 550, etc. The process/manipulated data 150 can be any combination of processed and/or manipulated data. Manipulation to the data can include overlaying a graphical user interface (GUI) on an image, zooming in on an image, and picture-in-picture of multiple sources including from other input modules. Manipulation to the data may also include image rotation, perspective correction, cropping, pan and scan, tilt and mirror in the horizontal and the vertical direction, and correcting for endoscope artifacts.

The control module 100 may also be configured to provide artificial horizon, wide angle lens support, adoption of camera perspective to surgeon perspective, intelligent image pan/scan controlled via surgeon movement.

It should be understood that the control module 100 may further process the image data 140 through hardware or software or some combination of hardware and software. For instance, control module 100 can implement a processor 110 running software 120 to further process the processed image data 140 into manipulated image data 150.

In order to be backwards and forwards compatible the control module 100 and input modules 200, 300, 400 may have to communicate what types of standard processed image data 140 they are compatible with. For instance, control module 100 may be compatible with several types of standard processed image data(e.g. HD or SD) and may have to communicate this compatibility with each input modules 200, 300, 400 in turn the input modules may have to communicate what types of standard processed image data 140 they are capable of transmitting. By communicating this information between the control module 100 and each input module 200, 300, 400 can settle on a type of standard processed image data 140 to communicate. Such functionality allows for the use of newer control modules with older input modules and newer input module with older control modules. For instance, if a input module was made for a newer imaging technology (e.g. HD) the input module may be capable of transmitting processed image data in HD or SD formats so that the new HD input module could function with an older SD control module. Likewise, if a user had a newer HD control module, the control module would be able to receive both HD and SD image data such that the HD control module would be backwards compatible with SD input modules.

In certain embodiments, the control module 100 is connected to, for example, an Intranet, the Internet and/or the like. In certain embodiments, the input modules 200, 300, 400 and/or the control module 100 includes WI-FI and/or a way to receive information directly from the Internet, either wired or wirelessly. In certain embodiments, any of the input modules may wirelessly connect to a related camera.

In certain embodiments, upon connection of control module 100 to, for example, input module 200 an input module identifier/program stored on input module 200 may be transmitted to the control module. It is contemplated that the input module identifier may comprise discrete data or may comprise a program that provides information relating to the input module 200 to the control module 100. In addition, it is contemplated that the control module 100 may also transmit a control module identifier/program stored on the control module 100 to the input module 200. It is contemplated that the control module identifier may comprise discrete data or may comprise a program that provides information relating to the control module 100 to the input module 200.

In certain embodiments, the control module 100 may send commands to the input module 200, which may include, for example, adjusting color balance, light, focal distance, resolution, zoom, focus, shading, and other optical characteristics if the input is a camera video or video endoscope. Input module 200 may then generate and transmit processed image data 140 to control module 100.

While the invention has been specifically described in connection with certain specific embodiments thereof, it is to be understood that this is by way of illustration and not of limitation, and that various changes and modifications in form and details may be made thereto, and the scope of the appended claims should be construed as broadly as the prior art will permit.

The description of the invention is merely exemplary in nature, and, thus, variations that do not depart from the gist of the invention are intended to be within the scope of the invention. Such variations are not to be regarded as a departure from the spirit and scope of the invention.

What is claimed is:

1. A modular endoscopic video system comprising:
a first camera from a first family of cameras, said first camera providing a first type image data;
a second camera from a second family of cameras, said second camera providing a second type image data;
a first input module releasably connected to said first camera with a communications cable, said first input module supporting functions of the first family of cameras, said first input module receiving the first type image data from said first camera and converting the first type image data to a first standard type image data;

a second input module releasably connected to said second camera with a communications cable, said second input module supporting functions of the second family of cameras, said second input module receiving the second type image data from said second camera and converting the second type image data to a second standard type image data;

a control module disposed external to the first and second input modules and releasably connected to each of said first input module and said second input module with a communications cable, said control module receiving the first and second standard type image data transmitted from said first input module and said second input module;

said control module providing a user interface, said user interface having controls for manipulating the first and second standard type image data into manipulated image data; and said control module connected to at least one display, the at least one display receiving and displaying the manipulated image data;

wherein for each of the first input module and second input module, upon connection to the control module, said control module is configured to communicate to the respective input module a plurality of types of standard processed image data the control module is compatible with, the respective input module is configured to communicate to said control module a plurality of types of standard processed image data the respective input module is configured to transmit, and said control module and said respective input module are configured to, by said communicating, settle on a type of standard processed image data to transmit.

2. The modular imaging system of claim 1, wherein the first type image data and the second type image data being at least in part differentiated by at least one of: aspect ratio, timing, pixel rate, pixel resolution, and pixel encoding.

3. The modular imaging system of claim 1, wherein said manipulated image data is at least one of: zoom, image rotation, picture-in-picture and graphical user interface overlay.

4. The modular imaging system of claim 1, wherein the first type image data is digital and the second type image data is analog.

5. The modular imaging system of claim 1, wherein the first type image data is high definition digital, the second type image data is high definition analog.

6. The modular imaging system of claim 1, further comprising:
a third camera, said third camera providing a third type image data; and
a third input module connected to said third camera and said control module, said third input module receiving the third type image data, converting the third type image data to a third standard type image data and transmitting the third standard type image data to said control module.

7. The modular imaging system of claim 1, further comprising:
an auxiliary input device, said auxiliary input device providing an auxiliary type image data; and
an auxiliary input module connected to said auxiliary input device and said control module, said auxiliary input module receiving the auxiliary type image data, converting the auxiliary type image data to a standard type image data and transmitting the standard type image data to said control module.

8. The modular imaging system of claim 7, wherein said auxiliary input device is at least one of: a personal computer, a room camera, a CCU, and a 3G-SDI source.

9. A method for providing a modular video imaging system, the method comprising the steps of:
providing a control module configured to process image data,
providing a first input module disposed external to the control module and releasably connectable to said control module with a communications cable, said first input module supporting functions of a first family of cameras, said first input module being connected to a first camera from said first family with another communications cable and configured to receive a first type image data from the first camera, process said first type image data into a first standard type image data, and transmit said first standard type image data to said control module; and
providing a second input module disposed external to the control module and releasably connectable to said control module with a communications cable, said second input module supporting functions of a second family of cameras, said second input module being connected to a second camera from said second family with another communications cable and configured to receive a second type image data from the second camera, process said second type image data into a second standard type image data, and transmit said second standard type image data to said control module;
wherein for each of the first input module and second input module, upon connection to the control module, said control module is configured to communicate to the respective input module a plurality of types of standard processed image data the control module is compatible with,
the respective input module is configured to communicate to said control module a plurality of types of standard processed image data the respective input module is configured to transmit, and
said control module and said respective input module are configured to, by said communicating, settle on a type of standard processed image data to transmit.

10. The method of claim 9, further comprising the step of:
providing a third input module disposed external to the control module and releasably connectable to said control module, said third input module configured to receive a third type image data, process said third type image data into a third standard type image data, and transmit said third standard type image data to said control module.

11. The method of claim 10, further comprising the step of:
providing a fourth input module disposed external to the control module and releasably connectable to said control module, said fourth input module configured to receive a fourth type image data, process said fourth type image data into a fourth standard type image data, and transmit said fourth standard type image data to said control module.

12. The method of claim 9, wherein said first type image data and said second type image data being at least in part differentiated by at least one of: aspect ratio, timing, pixel rate, pixel resolution, and pixel encoding.

13. The method of claim 10, wherein said first type image data, said second type image data and said third type image data are at least in part differentiated by at least one of: aspect ratio, timing, pixel rate, pixel resolution, and pixel encoding.

14. The method of claim 11, wherein said first type image data, said second type image data, said third type image data and said fourth type image data are at least in part differentiated by at least one of: aspect ratio, timing, pixel rate, pixel resolution, and pixel encoding.

15. The method of claim 9, wherein said control module manipulates said first and second standard type image data into manipulated image data.

16. The method of claim 15, wherein said manipulated image data is at least one of: zoom, image rotation picture-in-picture and graphical user interface overlay.

17. The modular imaging system of claim 15, further comprising a display connectable to said control module, said display configured for displaying said manipulated image data.

18. A modular video imaging system comprising:
a control module configured to receive processed image data,
a first input module disposed external to the control module and releasably connected to said control module with a communications cable, said first input module supporting functions of a first family of cameras, said first input module being connected to a first camera from said first family with another communications cable and configured to receive a first type image data from the first camera, process the first type image data into a first processed image data, and transmit said first processed image data to said control module;
wherein upon connection of the first input module to the control module, said control module is configured to communicate to said first input module a plurality of types of standard processed image data the control module is compatible with,
said first input module is configured to communicate to said control module a plurality of type of standard processed image data the first input module is configured to transmit, and
a first input module identifier stored in the first input module is transmitted to the control module and a control module identifier stored in the control module is transmitted to the first input module so that the first input module and the control module settle on a type of standard processed image data to transmit therebetween.

19. The modular imaging system of claim 18, further comprising:
a second input module connectable to said control module, said second input module configured for receiving a second type image data and processing the second type image data into a second processed image data for transmission to said control module.

20. The modular imaging system of claim 19, further comprising:
a third input module connectable to said control module, said third input module configured for receiving a third type image data and processing the third type image data into a third processed image data for transmission to said control module.

21. The modular imaging system of claim 20, further comprising:
a fourth input module connectable to said control module, said fourth input module configured for receiving a fourth type image data and processing the fourth type image data into a fourth processed image data for transmission to said control module.

22. The modular imaging system of claim 19, wherein the first type image data and the second type image data being at least in part differentiated by at least one of: aspect ratio, timing, pixel rate, pixel resolution, and pixel encoding.

23. The modular imaging system of claim 20, wherein the first type image data, the second type image data, and the third type image data are at least in part differentiated by at least one of: aspect ratio, timing, pixel rate, pixel resolution, and pixel encoding.

24. The modular imaging system of claim 21, wherein the first type image data, the second type image data, the third type image data, and the fourth type image data are at least in part differentiated by at least one of: aspect ratio, timing, pixel rate, pixel resolution, and pixel encoding.

25. The modular imaging system of claim 18, wherein said control module manipulates said first processed image data into manipulated image data.

26. The modular imaging system of claim 25, wherein said manipulated image data is at least one of: zoom, image orientation, image rotation, picture-in-picture and graphical user interface overlay.

27. The modular imaging system of claim 25, further comprising at least one display connectable to said control module, said at least one display configured for displaying said manipulated image data.

28. The modular imaging system of claim 18, further comprising at least one display connectable to said control module, said at least one display configured for displaying said first processed image data.

29. The modular imaging system of claim 18, further comprising an output connectable to said control module, said output being at least one of: a storage device, a personal computer, and a printer.

30. The modular imaging system of claim 19, wherein the first type image data is digital and the second type image data is analog.

31. The modular imaging system of claim 20, wherein the first type image data is high definition digital, the second type image data is high definition analog and the third type image data is standard definition analog.

32. The modular imaging system of claim 21, wherein the first type image data is high definition digital, the second type image data is high definition analog, the third type image data is standard definition analog, and the fourth type image data is one of: 3G SDI, DVI, S-Video and VGA.

* * * * *